United States Patent [19]
Linden

[11] Patent Number: 4,796,987
[45] Date of Patent: Jan. 10, 1989

[54] DIGITAL DISPLAY FOR HEAD MOUNTED PROTECTION

[76] Inventor: Harry A. Linden, 146 S. Sierra Vista, Santa Barbara, Calif. 93108

[21] Appl. No.: 35,219

[22] Filed: Apr. 7, 1987

Related U.S. Application Data

[63] Continuation of Ser. No. 683,813, Dec. 20, 1984, abandoned.

[51] Int. Cl.⁴ .............................................. G02C 1/00
[52] U.S. Cl. ..................................... 351/158; 351/43
[58] Field of Search ............... 351/158, 43, 51; 2/426, 2/428

[56] References Cited

U.S. PATENT DOCUMENTS

| | | | |
|---|---|---|---|
| 3,712,714 | 1/1973 | Uyeda et al. | 351/43 |
| 4,202,607 | 5/1980 | Washizuka et al. | 350/338 |
| 4,361,384 | 11/1982 | Bosserman | 350/174 |

Primary Examiner—Rodney B. Bovernick

[57] ABSTRACT

The preferred embodiment provides a stopwatch mounted in a lens, goggle, mask or shield for use by a swimmer or other goggle wearer to observe elapsed time during, or countdown time prior to, an activity.

14 Claims, 1 Drawing Sheet

DIGITAL DISPLAY FOR HEAD MOUNTED PROTECTION

This is a continuing application of application Ser. No. 683,813, now abandoned, filed Dec. 20, 1984, titled "Digital Display for Head Mounted Protection"; inventor H. Linden.

BACKGROUND OF THE INVENTION

1. Field of the Invention

The present invention relates to head or face protection and, in particular, to head or face protection having a digital display.

2. Description of the Prior Art

Goggles and face shields are used in many activities for the protection of the face and eyes. Participants in a number of these activities where goggles or face shields are used for protection would also benefit from an easily and readily available method to visually read time, equipment monitoring gages or other functions that cannot normally be readily observed while engaging in the particular activity. One such activity where goggles or masks are commonly used is in swimming, including recreational, training and competitive swimming. A common practice in swimming, particularly while in training or conditioning, is the necessity to monitor time in both elapsed or countdown form. The present method of monitoring time is to observe a stop clock prior to initiating a predetermined sequence of events (countdown), commence elapsing time when the sequence is initiated, then observe the stop clock at the conclusion of the sequence (elapsed time). In most cases a desirable elapsed time for a sequence of events is predetermined and compliance with this desirable time is unknown until the conclusion of the sequence.

In many sports activities requiring training and conditioning, such as distance running, the progress of the runner can be monitored by observing a common wristwatch. In order for athletes to improve their performance and consistency, there is a need to observe time during the progress of a training sequence for conformity to the predetermined and desirable time. Therefore, there exists a need to monitor time during training, conditioning or competition. Accordingly, this invention provides a stopwatch mounted on or built into face protection, such as a pair of goggles, face mask or shield, to provide a visual monitoring of time.

SUMMARY OF THE INVENTION

The present invention provides head mounted protection. The protection includes a frame having a member that provides protection of a predetermined degree for at least a portion of the head adapted to be releasably mounted to the head of a wearer. Preferably, the frame includes an eye protector for providing eye protection of a predetermined degree. Apparatus is mounted to the frame for providing a digital display of a parameter. Apparatus is provided for focusing the display to an eye of the wearer. Preferably, the display is mounted to the eye protector. Also preferably, the display providing apparatus is a digital stopwatch.

The present invention also provides a resettable stopwatch or countdown timer that can be mounted to goggles, a face mask or a shield and is focused through an appropriate lens for viewing at a very close distance. Further, the watch is battery powered through a miniaturized solid-state circuit and digitally displayed through a transmissive liquid crystal display. Moreover, a means is provided through a push-button contact pad switch to provide reset, start and stop timing modes. The watch is sealed to prevent failure due to water leakage and may be mounted or built into any desirable location on the goggles.

An example for a mode of operation is for a swimmer, swimming in a 50 meter pool, and wishing to swim an 800 meter distance event and finish at a specified length of time, for instance eight minutes. The swimmer would set the goggle-mounted watch, preferably at a negative number such as minus five seconds. In preparing for the event the swimmer has predetermined desirable times or splits for each 50 or 100 meter portions of the 800 meter event, for simplicity assume one minute per 100 meters. The watch is then started and as the digits count down from minus five seconds through zero the swimmer starts the event. The progress for each 100 meters can be observed during the event and the swimmer increases or decreases in speed to maintain or exceed the anticipated finish time.

Accordingly, the present invention provides a digital readout that may be attached to or fabricated into head mounted protection, such as goggles, face masks or shields, to allow the wearer to monitor time during some function normally difficult or previously impossible to observe.

BRIEF DESCRIPTION OF THE DRAWINGS

The following detailed description of the preferred embodiment can be understood better if reference is made to the attached drawings in which.

DETAILED DESCRIPTION OF THE PREFERRED EMBODIMENTS

Figure 1:
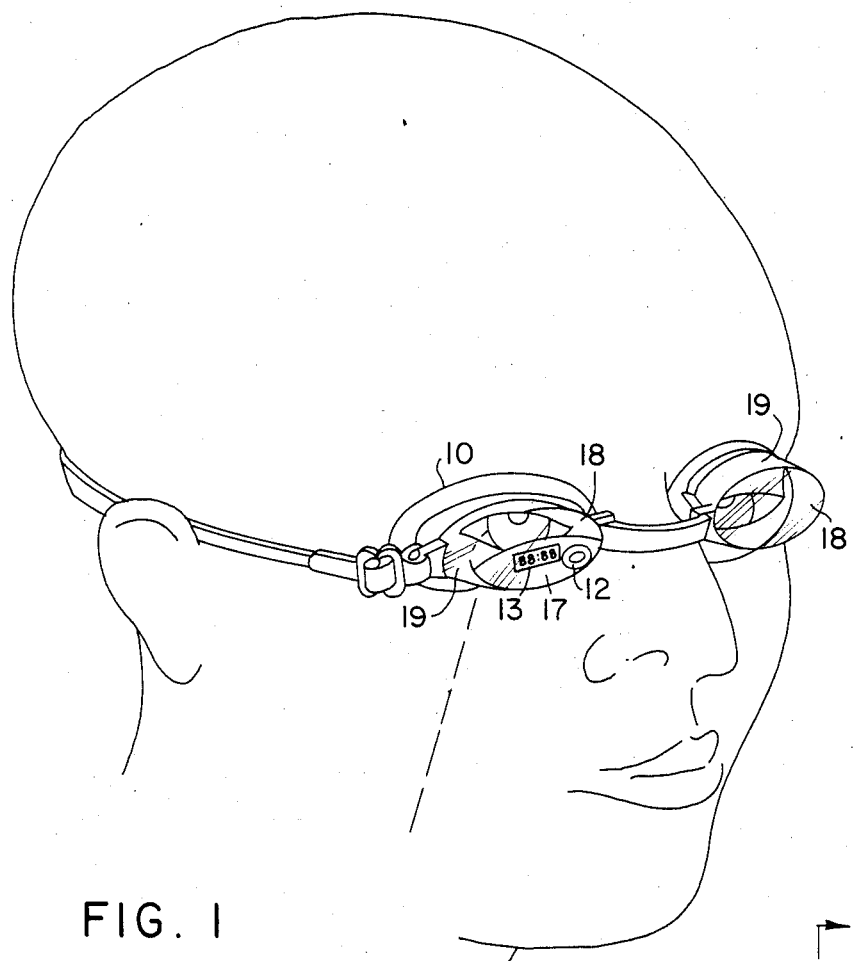
FIG. 1 is a view of a person wearing goggles with an attached digital readout stopwatch.
Figure 2:
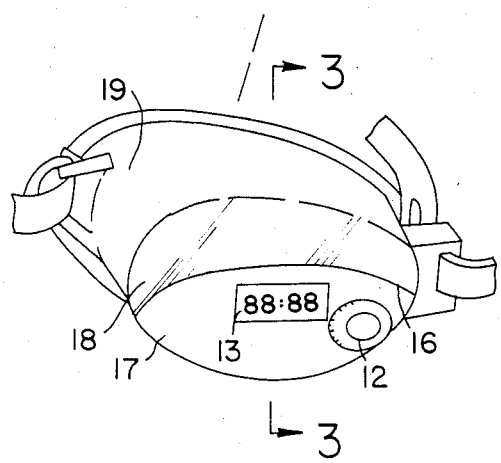
FIG. 2 is a developed exterior view of a goggle lens with a stopwatch.
Figure 3:
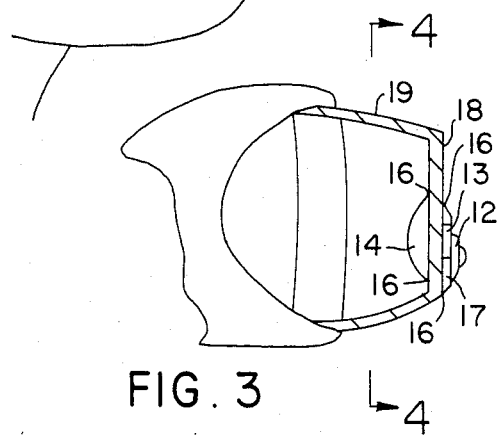
FIG. 3 is a sectional view of the goggle lens shown in FIG. 2 showing the focusing lens and the transmissive liquid crystal display taken along the line A—A.
Figure 4:
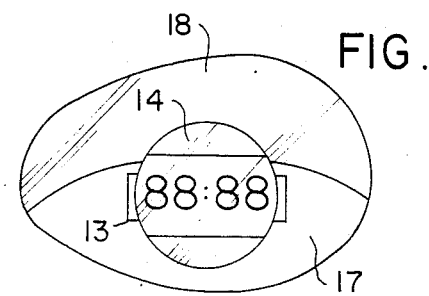
FIG. 4 is an interior view showing the digital readout with ambient back light shown through the focusing lens taken along the line B—B.

FIGS. 1, 2, 3 and 4 show a goggle 10 mounted with a stopwatch 17 that is the preferred embodiment of the present invention. Goggle 10 includes a frame 19 with an integral transparent lens 18 onto which a digital stopwatch 17 is mounted by a sealant 16 to the exterior and a focusing lens 14 is mounted to the interior.

The mounted stopwatch 17 is of a size and mounted in such a way to lens 18 that normal vision to the wearer is not impaired. Also, focusing lens 14 is mounted to transparent goggle lens 18 by sealant 16 so that vision through the transparent goggle lens 18 is not entirely obscured and aligned so that digital display 13 is centered within the focusing lens 14. The foregoing description of watch 17, transparent goggle lens 18, focusing lens 14, digital display 13 and stop, start and reset button 12 can be fabricated as an integral portion of the goggles 10.

The stopwatch 17 consists of an appropriate conventional electric circuit for driving a transmissive or transparent liquid crystal display 13. The internal electric circuit is programmed to accept external signals through the reset button 12. In operation, the reset button 12 is depressed, causing the watch circuit to display a preprogrammed time, such as zero time, or a negative time, such as minus five or ten seconds. Upon a second activation of switch 12 the display 13 systematically shows a progressive time in seconds and minutes. The countdown or elapsed time is viewed by the wearer through focusing lens 14 as dark digits against an ambient or backlit background. The entire watch system 17 is positioned on the goggle lens 18 so as to cause minimal obstruction to the viewer's vision through the goggles. Hence, the viewer need only refocus the eye from a distance to the close-up digital display 13 with little or no alteration in the engaged activity. The power source for the watch is a small, low voltage battery that may be replaced after full energy discharge. The present invention incorporates presently available technologies of watch circuits, batteries, liquid crystal displays and lens to form a unique system.

What is claimed is:

1. A headgear comprising:
   a frame releasably securable to a wearer's head, said frame including a goggle portion for protecting the wearer's eyes from water;
   a liquid crystal digital display unit for indicating digital time parameters, said unit being secured to said goggle portion so as to be protected from water, said display unit being light-transmissive so as to permit viewing therethrough by the wearer, said display unit being readable by the wearer against an ambient background; and
   control means for controlling said display unit, said control means being accessible by the wearer when said frame is secured to the wearer.

2. A headgear comprising:
   a frame releasably securable to a wearer's head; and
   an information display secured to said frame so as to be within the wearer's direct view when said frame is secured to the wearer's head, said display being light-transmissive so as to permit viewing therethrough by the wearer, said display being readable by the wearer against an ambient background, said frame including a goggle portion for deflecting water from the wearer's eyes, wherein said display is mounted on said goggle portion so as to be protected from water, and said display is a liquid crystal digital type.

3. The headgear of claim 2 wherein said goggle portion includes one protective lens for each eye and said display is mounted on a lens.

4. A headgear comprising:
   a frame releasably securable to a wearer's head; and
   an information display secured to said frame so as to be within the wearer's direct view when said frame is secured to the wearer's head, said display being light-transmissive so as to permit viewing therethrough by the wearer, said display being mounted behind a transparent focusing lens having a focal length suitable for permitting direct reading therethrough of the display, said display being readable by the wearer against an ambient background, wherein said display includes a time indicator.

5. The headgear of claim 1 wherein said time indicator includes a disposable battery interconnected to said information display, said disposable battery powering said information display to indicate at least one digital time parameter.

6. The headgear of claim 4 wherein said time indicator includes a switch portion which is readily manually accessible by the wearer when said frame is secured to the wearer's head, said switch portion controlling said time indicator.

7. The headgear of claim 6 wherein said time indicator is a stopwatch.

8. The headgear of claim 7 wherein said stopwatch can be set at a negative number.

9. The headgear of claim 4 wherein said frame includes eye protectors, said time indicator being secured to at least one of said eye protectors.

10. The headgear of claim 9 wherein the dimensions of said time indicator are approximately 14×17 mm, said time indicator including at least three digits arranged to display two digits of seconds and at least one digit of minutes.

11. A headgear comprising:
    a frame releasably securable to a wearer's head; and
    an information display secured to said frame so as to be within the wearer's direct view when said frame is secured to the wearer's head, said display being light-transmissive so as to permit viewing therethrough by the wearer, said frame including a lens having a focal length of no more than 20 mm and a width or diameter of no more than 25 mm, said display being mounted behind said lens.

12. The headgear of claim 11 wherein said frame includes two lenses, each lens protecting one of the wearer's eyes.

13. A headgear comprising:
    a frame releasably securable to a wearer's head, said frame including means for protecting the wearer's eyes, said means permitting viewing therethrough by the wearer; and
    an information display attached to said frame so as to be located when secured proximate to the wearer's eyes, said display being directly viewable by the wearer, said frame being mounted behind a transparent focusing lens having a focal length suitable for permitting direct reading of said display by the wearer through said focusing lens, said display being predeterminedly sized and positioned on said frame to cause minimal visual obstruction to the wearer when directly viewing through said means.

14. The headgear of claim 13 wherein said means for protecting include a goggle portion having at least one protective lens for deflecting water from the wearer's eyes, said information display being mounted on said frame so as to be protected from water.

* * * * *